the production of collagen from animal intestines etc. It is characterized in that the starting material is mixed with ice-water at a pH of 5,5, that the mixture is disintegrated and then heated to 40°–42° C. and hydrolysed at a pH of 10,5 using a proteolytic enzyme. After finishing of the hydrolyses pH is regulated to 5,5 and the collagen is separated and collected. The invention also encloses collagen produced through the process and a number of new application areas for collagen.

United States Patent [19]

Sjölander

[11] Patent Number: 5,411,887
[45] Date of Patent: May 2, 1995

[54] METHOD FOR THE PRODUCTION OF COLLAGEN: COLLAGEN PRODUCED THROUGH THE METHOD AND USE OF COLLAGEN

[75] Inventor: Einar Sjölander, Hisings Kärra, Sweden

[73] Assignee: Collagen Casing Einar Sjolander AB, Sweden

[21] Appl. No.: 133,083

[22] PCT Filed: Mar. 26, 1992

[86] PCT No.: PCT/SE92/00192
§ 371 Date: Oct. 5, 1993
§ 102(e) Date: Oct. 5, 1993

[87] PCT Pub. No.: WO92/17503
PCT Pub. Date: Oct. 15, 1992

[30] Foreign Application Priority Data

Apr. 5, 1991 [SE] Sweden .................. 9100999

[51] Int. Cl.⁶ .............. C07K 1/14; C07K 14/435; C07K 14/78; A61K 38/39
[52] U.S. Cl. .................. 435/273; 435/41; 435/68.1; 530/356
[58] Field of Search ............ 435/41, 273, 68.1; 530/356

[56] References Cited

U.S. PATENT DOCUMENTS

| | | | |
|---|---|---|---|
| 4,066,083 | 1/1978 | Ries | 435/273 |
| 4,220,724 | 9/1980 | Berg et al. | 435/273 |
| 4,331,766 | 5/1982 | Becker et al. | 435/273 |
| 4,389,487 | 6/1983 | Ries | 435/273 |

FOREIGN PATENT DOCUMENTS

| | | |
|---|---|---|
| 2023613 | 1/1980 | United Kingdom . |
| WO81/03261 | 11/1981 | WIPO . |
| WO86/00501 | 1/1986 | WIPO . |

OTHER PUBLICATIONS

Derwent ABS 81-93071D/50 WO8103261, Sjoelander Nov. 26, 1981.
Derwent AB 93-312039/40 EP-564786, Coleman et al Oct. 1993.

Primary Examiner—Herbert J. Lilling
Attorney, Agent, or Firm—Lerner, David, Littenberg, Krumholz & Mentlik

[57] ABSTRACT

The present invention relates to a process for the production of collagen from animal intestines etc. It is characterized in that the starting material is mixed with ice-water at a pH of 5,5, that the mixture is disintegrated and then heated to 40°–42° C. and hydrolysed at a pH of 10,5 using a proteolytic enzyme. After finishing of the hydrolyses pH is regulated to 5,5 and the collagen is separated and collected. The invention also encloses collagen produced through the process and a number of new application areas for collagen.

14 Claims, No Drawings

METHOD FOR THE PRODUCTION OF COLLAGEN: COLLAGEN PRODUCED THROUGH THE METHOD AND USE OF COLLAGEN

TECHNICAL FIELD

The present invention relates to an improved way for the production of collagen and collagen produced through the process and the use of collagen in different areas.

PRIOR ART

Collagen is a fibre formed substance consisting of 18 amino-acids and it provides the main part of the intestines and stomach of animals but is also included in other parts of the animal body, for example in the interial part of the skin in the shape of hide, in lunges and udders etc. One has earlier primarily used the collagen in its native shape, mostly as sausage skin made from cleaned intestines. During resent years one has also produced collagen in its clean shape starting from the above said body parts of animals and used this clean collagen for different purposes such as artificially made sausage skins, additional agents for treatment articles, surgery threads etc. A known way of producing collagen is described in the Swedish Patent No. 8003876-3 in which a process is described that comprises cutting cleaned intestines etc. in stripes and pieces which are deep frozen and ground where upon they are subjected to the influence of an enzyme in a water solution whereby the aminoacids which do not provide a part of the collagen is hydrolysed so that insoluble remaining collagen can be removed and used after further treatment. Another process for producing collagen comprises the use of lime for separating the collagen fibrils. This process is time consuming and results also in that free collagen molecules are separated which impairs the properties of the end product.

TECHNICAL PROBLEM

It has since long been a desire to bring about a process which is better than the two above mentioned processes for the production of collagen. Thus, the first of said above mentioned processes includes that one has to freeze this disintegrated starting materials which is circumstantially and expensive and that one has to carry out the hydrolysis at a relatively low pH, approximately 8, using a relatively week enzyme during a period of 2–5 hours. This process is both costly and time consuming.

By the second of the above mentioned processes lime has to be added which results in a lower grade end product at the same time as an extended process will be necessary.

THE SOLUTION

By the present invention one has solved the problems connected with the above mentioned processes and brought about a process for the production of collagen from by-products of slaughtered and cut animals, such as intestines, stomach etc. which is characterized by the following process steps:

a) the starting materials are cleaned and immersed in ice-water, pH being regulated to approximately 5,5, b) the mixture of starting materials and ice-water is ground whereupon further water is added so that the ground mixture contains approximately equal weight parts of starting materials and water, c) the mixture is heated to 40°–42 °C. and pH is regulated to at most 11, preferably 10,5 whereupon a proteolytic enzyme, for instance alkalas in an amount corresponding to 60 Anson-units per kilo solid substance is added so that hydrolysis of other proteins than collagen is carried out during maintaining the pH value by adding alkali until the hydrolyses is completed and alkali is no more consumed, d) pH is regulated to 5,5 by adding an acid whereupon e) separated collagen is collected.

According to the invention it is suitable that pH in steps a) and d) is regulated by means of hydrochloric acid, citric acid or lactic acid.

The hydrolysing is carried out according to the invention during a period of time of $1\frac{3}{4}$ hours to $3\frac{1}{2}$ hours while adding sodium hydroxide as alkali.

According to the invention the separated collagen can be collected by sifting, cleaning with water at about 40° C. and centrifugation or decanting. Only one wash with water is sufficient.

It is according to the invention further suitable that the collagen is homogenized after being collected at pH c:a 3 by alternatively adding acids and water while mechanically treating until the desired end concentration of collagen is obtained.

It is according to the invention suitable for obtaining a clear transparent film from the completed collagen that it is mixed with reduction agents, such as ascorbic acid and sodium sulphite in an amount of up to 2 weight per cent, and cross-binding agents for example glutaraldehyde in an amount of approximately 0,1 weight per cent and 5–10 weight per cent glycerol as softener, all calculated on solid collagen.

The invention comprises also collagen produced by the process according to the above description and use of collagen as a binder for meat products, as a film for packing of food and medicines, as a carrier by the production of colours, as artificial leather, as a gel for treatment of wounds, as a cover on chips for electronic purposes and as covers within the paper industry.

The raw materials that can be used in the process according to the invention is primarily such materials that come from the digesting organs of the animals such as rumen, fourth stomach, second stomach, intestines and lunges and udder from ruminants. Also the large intestine from pigs can be used.

When using an intestine this is first emptied by having a machine squeezing out the content and the inner part of the intestines called the mucosa by squeezing between rubber rollers. Any limitation of the assortment of raw materials does not exist and all such that comprise collagen in sufficient amount can be used. The raw materials are pretreated advantageously by removing fat, the so called mesentery and the like.

The cleaned starting materials are then mixed with ice-water which suitably have an addition of acetic acid so that a pH of about, 5,5 is obtained. Herethrough the intestine is rapidly cooled and possible bacteria evolution will cease. One avoids to freeze the starting materials that can be transported and maintained in this condition before they are ground. This is important as the production of collagen only occurs at very few places and the starting materials have to be transported from the slaughter-houses to the collagen-factory.

At the collagen-factory pure water is added so that the starting materials are present in an amount of about 50 per cent by weight of the mixture. This is heated to 40°–42° C. when stirring and one adds sodium hydroxide so that pH is raised to 10,5 and the temperature adjusted to 40°–42° C. It is important that the temperature does not exceed this value as the collagen than will undergo crystalline changes and at still higher temperatures will change into gelatine. At the desired temperature and pH value the proteolytic enzymes are added which preferably consist of alkalas. At this high pH a strong concentration of enzymes can be added and the time for hydrolysing is therefore short, from 1½ hour to 3½ hours. During the hydrolyses the alkali is consumed so that alkali has to be added continuously maintaining a pH of 10,5. When the hydrolyses is completed, which is noticed by the fact that the pH does not sink any more when alkali is not added, the pH of the mixture is lowered to 5,5 by the addition of an acid, for example hydrochloric acid, acetic acid, citric acid or lactic acid. What occurs during the hydrolyses is that the alkalas is hydrolysing the proteins which are not a part of the collagen.

At pH 5,5 lumps are formed and a contraction of the collagen occurs. This depends on that the isoelectric point of the collagen is at pH about 5,5, which is generally known. In this shape it is preferable to separate the collagen suitably through a sift or the like.

The collagen is finally washed in water at a temperature of about 40° C. and is centrifugated or decanted. At the centrifugation the collagen normally gets a solids content of about 22 per cent and at the decantation about 30 per cent.

To use the collagen for the intended purpose it is preferable that it is homogenized which occurs through mechanical treatment in a vacuum mixer suitably with a dough hook or the like when acid such as hydrochloric acid or lactic acid is added together with water so that pH 3 and a desired concentration of collagen is obtained. After the homogenisation the collagen is set to ripen at a low temperature, normally 8°–10° C. during a period of time of 24 hours.

When the collagen shall be used for film forming, for example film in the shape of eatable sausage skin, a cross-linking agent for example glutaric aldehyde is added to the collagen in an amount of about 0,1 weight per cent and a softener in the shape of glycerol in an amount of 5–10 weight per cent. To obtain a film which is clear and transparent also an anti-oxidant such as ascorbic acid or sodium-bisulphate in an amount of up to 2 per cent by weight, preferably 0,02–0,1 per cent by weight should be added.

As a by-product from the collagen production animal pellets can be produced from the hydrolysing water by evaporation while adding vitamins, minerals, and taste agents or it can be used as wet fodder which then must be consumed rapidly so that putrefaction does not occur.

The proteolytic enzyme used consists preferably of Novos alkalas 2,6 which contains 60 Anson units per 25 millilitre. This alkalas is about 4 times stronger than earlier known varieties of alkalas. Together with the high pH-value during the hydrolyses it therefore gives a very rapid hydrolyses reaction, which in its turn means an economic advantage. This process also gives a product having a small fat content, which is of great importance for the succeeding film formation.

EXAMPLE:

6,5 kilogram cleaned pig intestines are immersed in ice-water having a pH of 5,5. The pH-value is regulated by means of acetic acid. The intestines and the ice-water are ground whereupon water is added so that a total amount of water plus intestines became 13 kilogram, that is 6,5 kilogram water and 6,5 kilogram cleaned pig intestines.

The mixture is stirred and heated to 40°–41° C. during addition of about 143 millilitre 4M NaOH until a pH of 10,5 was obtained. Thereafter a proteolytic enzyme in the shape of alkalas 2,6L from Novo in an amount of about 150 millilitre was added. pH was maintained constant at 10,5 during about 1½ hour at further addition of 4M NaOH so that the total amount NaOH became 253 millilitre.

After the hydrolysing the pH was lowered to 5,5 by the addition of hydrochloric acid. The collagen produced contracted and formed lumps.

The collagen was separated over a sift and washed in water at a temperature of 40° C. and a water amount of 6–7 kilogram during stirring. The washing time was 20–25 minutes. Collagen was then collected by centrifugation and was homogenized in a vacuum mixer with a suitable dough hook. During the homogenisation water and hydrochloric acid was added so that a pH of 3 and a solids content of 8 per cent was obtained. During the homogenisation the temperature of the collagen was not higher than 15°–18° C.

After the homogenisation the collagen was ripened during a period of time of 24 hours and at a temperature of 8°–10° C. whereupon it was sifted for removing of possible lumps or impurities in a special sift under pressure.

After addition of ascorbic acid, glutaric aldehyde and glycerol the collagen was extruded to a clear film.

By the present invention one has accordingly brought about an economic process which results in collagen having a very high quality and which can be used in a number of new areas such as declared above.

I claim:

1. A process for separating collagen from animal tissue comprising the steps of:
    immersing said collagen containing tissue in a mixture of frozen and liquid water, said mixture having a pH which is maintained at about 5.5;
    heating said collagen and water mixture to a temperature no higher than about 42 C while regulating the pH of said collagen and water mixture such that it does not exceed about 11;
    adding to said heated collagen and water mixture an amount of at least one proteolytic enzyme which is sufficient to hydrolyze protein in said tissue, other than said collagen;
    hydrolyzing said protein;
    adjusting the pH of the collagen and water mixture to about 5.5; and
    separating said collagen from said mixture.

2. The process of claim 1, further comprising the step of adding additional water to said collagen and water mixture until approximately 50% of the mixture by weight is tissue.

3. The process of claim 1 further comprising the step of said collagen and grinding said tissue prior to said heating step.

4. The process of claim 1 wherein, during said heating step, the pH is maintained at no more than about 10.5.

5. The process of claim 1 wherein, during said hydrolyzing step, the pH is maintained at no more than about 10.5.

6. The process of claim 1 wherein the amount of proteolytic enzyme added is about 60 Anson units per kilogram of solid.

7. The process of claim 1 further comprising the step of cleaning said tissue prior to said immersion step.

8. A process for separating collagen from animal tissue comprising the steps of:

providing clean collagen containing tissues;

immersing said collagen containing tissue in a mixture of frozen and liquid water, said mixture of frozen and liquid water not exceeding the weight of the collagen containing tissue added, while maintaining the pH of said mixture at about 5.5;

grinding said collagen and water mixture;

adding additional water if necessary to provide a mixture which is approximately 50% by weight water and 50% by weight collagen;

heating said collagen and water mixture to a temperature no higher than about 42 C while regulating the pH such that it is no higher than about 11;

adding to said heated collagen and water mixture an amount of a proteolytic enzyme which is sufficient to hydrolyze protein in said tissue other than said collagen and hydrolyzing said protein while maintaining said pH of said mixture;

lowering the pH of said mixture to about 5.5 following substantial completion of the hydrolysis reaction;

and separating said collagen from said mixture.

9. The process according to claims 1 or 8 wherein an acid selected from the group consisting of hydrochloric acid, citric acid or lactic acid is used to maintain said pH of said mixture at about 5.5.

10. The process of claims 1 or 8 where hydrolysis is carried out for a period of between 1.75 and 3.5 hours.

11. The process of claims 1 or 8 wherein said pH of said mixture is maintained at a level of at most 11 during said heating and hydrolysis step by the addition of sodium hydroxide.

12. The process of claims 1 or 8 wherein said collagen is collected by fixing and washing said collagen with water at about 40 C followed by centrifugation or decantation.

13. The process according to claim 12 wherein said collagen is homogenized after collection at a pH of about 3.

14. The process of claims 1 or 8 further comprising the steps of producing a clear transparent film by mixing the collected collagen with a reducing agent in the amount of about 2 weight percent, and a cross-linking agent in the amount of about 0.1 weight percent and a softener in an amount of about 5-10 weight percent based on said collagen, and extruding said film.

* * * * *

UNITED STATES PATENT AND TRADEMARK OFFICE
CERTIFICATE OF CORRECTION

PATENT NO. : 5,411,887
DATED : May 2, 1995
INVENTOR(S) : Sjölander

It is certified that error appears in the above-indentified patent and that said Letters Patent is hereby corrected as shown below:

Column 4, line 15, "$1^1/_2$" should read --$1^3/_4$--.

Signed and Sealed this

Twenty-ninth Day of August, 1995

Attest:

BRUCE LEHMAN

Attesting Officer      Commissioner of Patents and Trademarks